US00PP29846P2

(12) United States Plant Patent
Bacon

(10) Patent No.: US PP29,846 P2
(45) Date of Patent: Nov. 20, 2018

(54) PLUM TREE NAMED 'SUPLUMFIFTYONE'

(50) Latin Name: *Prunus salicina*
Varietal Denomination: Suplumfiftyone

(71) Applicant: Sun World International, LLC, Bakersfield, CA (US)

(72) Inventor: Terry A. Bacon, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 0 days.

(21) Appl. No.: 15/732,688

(22) Filed: Dec. 14, 2017

(51) Int. Cl.
*A01H 5/08* (2018.01)

(52) U.S. Cl.
USPC ..... Plt./184
CPC ..... *A01H 5/0862* (2013.01)

(58) Field of Classification Search
USPC ..... Plt./184
See application file for complete search history.

*Primary Examiner* — Kent L Bell
(74) *Attorney, Agent, or Firm* — Knobbe, Martens, Olson & Bear, LLP

(57) ABSTRACT

A new and distinct plum tree variety, *Prunus salicina*, cv. 'Suplumfiftyone' is characterized by having large fruit with dark red flesh. The fruit of the new variety 'Suplumfiftyone' is also moderately firm, juicy and has a mild sweet flavor. The date of the harvest of the fruit of the new variety is later than for 'Black Splendor' (unpatented). The fruit of the new variety 'Suplumfiftyone' ripens with nearly same timing as the fruit of 'Friar' (unpatented) but has a dark red flesh compared to yellow-colored flesh for the fruit of 'Friar'.

1 Drawing Sheet

Latin name of the genus and species claimed: *Prunus salicina.*

Variety denomination: 'Suplumfiftyone'.

BACKGROUND AND SUMMARY OF THE INVENTION

This invention relates to the discovery and asexual propagation of a new and distinct variety of plum, *Prunus salicina* cv. 'Suplumfiftyone'. The new variety was first originated by hybridization in July 2013 by Terry A. Bacon as breeder number 'PL1617RB'.

The new variety 'Suplumfiftyone' is characterized by having large fruit with dark red flesh. The fruit of the new variety 'Suplumfiftyone' is moderately firm, juicy and has a mild sweet flavor.

The seed parent is 'PL888RB' (unpatented breeding selection), and the pollen parent is bulk pollen of several midseason plums. The parent varieties were first crossed in February 2010, with the date of first sowing being February 2011, and the date of first flowering being February 2013. The new plum variety 'Suplumfiftyone' was first asexually propagated by Terry Bacon near Wasco, Kern County, Calif. in February 2014 by dormant grafting.

The new variety 'Suplumfiftyone' is similar to its seed parent 'PL888RB' in that both varieties have a red flesh. The new variety 'Suplumfiftyone' differs from 'PL888RB' in that the fruit of the new variety is larger than the fruit of 'PL888RB', at 170 g compared to 129 g for 'PL888RB'. The fruit of the new variety 'Suplumfiftyone' also ripens about 2 weeks earlier than that of 'PL888RB'.

The fruit of the new variety 'Suplumfiftyone' ripens about the same time as the fruit of the variety 'Friar' (unpatented), but the fruit of the new variety 'Suplumfiftyone' has a red flesh compared to yellow flesh for 'Friar'. The fruit of the new variety 'Suplumfiftyone' has a red flesh that is similar to the flesh of the fruit of the variety 'Black Splendor' (unpatented), but the fruit of the new variety 'Suplumfiftyone' starts ripening about 43 days later than that of 'Black Splendor'.

The new variety 'Suplumfiftyone' has been shown to maintain its distinguishing characteristics through successive asexual propagations by, for example, cuttings and grafting.

BRIEF DESCRIPTION OF THE PHOTOGRAPH

The accompanying color photographic illustration FIG. 1 shows typical specimens of the foliage and fruit of the present new plum variety 'Suplumfiftyone'. The illustration shows the upper and lower surface of the leaves, a view of the fruit as a whole, the stone as a whole, and a sectional view of a fruit divided across its suture plane to show flesh color, pit cavity and the stone remaining in place. The photographic illustration was taken shortly after being picked and the colors are as nearly true as is reasonably possible in a color representation of this type. The photographs depict fruit and vegetative growth from a four year old tree.

DETAILED DESCRIPTION OF THE PREFERRED EMBODIMENT

Throughout this specification, color names beginning with a small letter signify that the name of that color, as used in common speech is aptly descriptive. Color names beginning with a capital letter designate values based upon The R.H.S. Colour Chart published by The Royal Horticultural Society, London, England, 1986.

The descriptive matter which follows pertains to four year old plants of 'Suplumfiftyone' grown in the vicinity of Wasco, Kern County, Calif., during 2017 and is believed to apply to plants of the variety grown under similar conditions of soil and climate elsewhere.

TREE

General: (Measurements taken on four year old trees unless otherwise noted.).

*Size*.—Medium, reaches a height of approximately 3 meters including normal pruning.

*Habit*.—Spreading.

*Vigor*.—Medium, top shoot growth of at least 1 meter during the growing season.

*Productivity*.—Very Productive.

*Bearer*.—On spurs and long shoots.

*Fertility*.—Self-incompatible; requires pollinator.

*Hardiness*.—Hardy in all fruit growing areas of California. Winter chilling requirement is approximately 550 hours at or below 7.2° C.

*Disease resistance/susceptibility*.—Under close observation in Kern County, Calif., no particular plant/fruit disease resistance/susceptibility has been observed.

*Insect resistance/susceptibility*.—Under close observation in Kern County, Calif., no particular plant/fruit insect resistance/susceptibility has been observed.

Trunk: (Measurements at approximately 30 cm above soil line on mature trees).

*Diameter*.—Approximately 14 cm.

*Texture*.—Medium shaggy, increasing with the age of the tree.

*Trunk color*.—About Dark Greyed-Orange 166A, becoming darker with age.

Branches: (Measurements at approximately 90 cm above soil line).

*Size*.—Diameter approximately 8 cm.

*Texture*.—Medium shaggy, increasing with age.

*Color*.—About Medium Grey 201B with highlights of about Medium Greyed-Brown 199B, becoming darker with age.

*Lenticels*.—Present.

*Lenticels density*.—Plentiful, about 12/cm$^2$.

*Lenticels color*.—About Light Grey 201D.

*Lenticels dimensions*.—Length: approximately 3 mm. Width: approximately 1 mm.

Flowering shoots: (Data taken in September at mid-point of current season growth.).

*Size*.—Average diameter approximately 5 mm.

*Color*.—Topside: About Dark Greyed-orange 176A. Underside: About Dark Greyed-Orange 176A.

*Internode length*.—Approximately 2.5 cm. Midway on flowering shoot.

*Flowering shoot lenticels*.—Plentiful. Color: About Light Grey 201D. Diameter: Approximately 0.5 mm.

*Flowering shoot vegetative buds*.—Size: Medium, approximately 1.5 mm×2.5 mm. Shape: Conical. Bud shape at apex: Acute. Color: About Dark Greyed-Orange 177A.

*Flowering shoot flower buds*.—Shape: Acute. Dimensions: Approximately 1.5 mm×2.8 mm. Color: About Dark Greyed-Orange 177A. Distribution: 2-6 buds, generally on spurs and one year old shoots.

*Ratio of flowering buds to vegetative buds*.—2-6 flower buds to 1 vegetative bud.

*Anthocyanin intensity on upper side of shoot*.—Strong.

*Spur length*.—Medium, usually 10 mm.

*Position of vegetative bud in relation to shoot*.—Slightly held out.

FOLIAGE

Leaves: (Data taken in September on fully expanded leaves at mid-point of the current season growth.).

*Average length*.—Medium; approximately 8 cm without petiole.

*Average width*.—Medium; approximately 3.6 cm.

*Length/width ratio*.—Moderately elongated, about 2.2:1.

*Color*.—Upper surface: About Dark Green 136A. Lower surface: About Medium Green 139B.

*Shape*.—Elliptic.

*Tip*.—Cuspidate.

*Base*.—Acuminate.

*Margin*.—Crenate.

*Venation*.—Pinnately net veined.

*Vein color*.—About Medium Green 138B with highlights of Medium Greyed-Orange 176C where exposed to sun.

*Surface texture*.—Smooth upper and lower surfaces.

*Shape in the cross section*.—Concave.

*Angle at apex*.—Right angled.

*Profile*.—Up folded.

*Leaf blade tip*.—Curved downwardly.

*Undulation of margin*.—Slight.

*Glossiness of upper side*.—Weak.

*Density of pubescence of lower side*.—Absent or very sparse.

Petiole:

*Average length*.—Approximately 12 mm.

*Average diameter*.—Approximately 2 mm.

*Color*.—About Medium Green 138B with highlights of Medium Greyed-Orange 176C where exposed to sun.

Stipules:

*Number/leaf bud*.—Usually one.

*Typical length*.—Approximately 8 mm.

*Color*.—About Dark Greyed-Orange 166A.

*Persistence*.—Falls off.

Leaf glands:

*Average number*.—Approximately 0-2.

*Form*.—Globose.

*Diameter*.—Approximately 0.3 mm.

*Color*.—About Medium Greyed-Yellow 162A becoming Dark Greyed-Orange 166A over time.

FLOWERS

General:

*Time of beginning of flowering*.—Medium for the San Joaquin Valley, Calif.

*Flower blooming period*.—First bloom: Approximately February 22 in Wasco, Calif. Full bloom: Approximately February 26 in Wasco, Calif.

*Location of first bloom*.—Tips of one year old shoots.

*Location of full bloom*.—Central part of the tree canopy.

*Duration of bloom*.—Approximately 10 days.

*Diameter of fully opened flower*.—Medium, approximately 2 cm.

*Flower form*.—Showy.

Pedicels:
*Length*.—Approximately 10 mm.
*Diameter*.—Approximately 1.2 mm.
*Color*.—About Light Green 139D.
*Pubescence*.—Absent.
Petals:
*Number*.—5.
*Arrangement*.—Overlapping.
*Color*.—About White 155A.
*Length*.—Medium, approximately 8 mm.
*Width*.—Approximately 7 mm.
*Shape*.—Circular.
*Apex shape*.—Rounded.
*Base shape*.—Narrows at point of attachment.
*Surface texture*.—Smooth.
*Undulation of margins*.—Medium.
*Frequency of flowers with double petals*.—None.
*Claw*.—Absent.
Sepals:
*Number*.—5.
*Length*.—Approximately 4 mm.
*Diameter*.—Approximately 3 mm.
*Shape*.—Medium ovate.
*Color*.—About Light Green 139D.
*Surface texture*.—Smooth.
*Margins*.—Undulating.
*Positioning*.—Adpressed to petals.
*Frequency of flowers with double sepals*.—None.
Stamens:
*Number*.—Usually 25-32, usually 28.
*Average length*.—Variable, ranging from 3 mm to 10 mm.
*Filament color*.—About White 155A.
*Flower pollen color*.—About Light Yellow-Orange 18C.
*Position*.—Perigynous.
Pistil:
*Average length*.—Approximately 3-4 mm.
*Ovary diameter*.—Approximately 2 mm.
*Pubescence*.—Absent.
*Stigma extension in comparison to anthers*.—Usually above.
*Style frequency of supplementary pistils*.—Few.
Receptacle:
*Depth*.—Medium, approximately 4 mm.
*Pubescence of inner surface*.—Absent.
*Pubescence of outer surface*.—Absent.

FRUIT

General: (Description taken near Wasco, Kern County, Calif.).
Ripening:
*Time of beginning of fruit ripening*.—Medium, mid-season.
*Date of first pick*.—Approximately July 24.
*Date of last pick*.—Approximately August 3.
*Maturity when described*.—Firm.
*Position of maximum diameter*.—Towards the middle.
Size:
*Height*.—Tall, approximately 68 mm.
*Diameter in line with suture plane*.—Approximately 68 mm.
*Diameter perpendicular to suture plane*.—Broad, approximately 68 mm.
*Average weight*.—Approximately 170 gm.
Peduncle:
*Length of stem*.—Short, approximately 7 mm.
*Diameter of stem*.—Approximately 3 mm.
*Color of stem*.—About Light Green 139D.
Shape:
*Viewed from apex*.—Circular.
*Viewed in-line with suture*.—Circular.
*Viewed from side, perpendicular to suture*.—Circular.
*Symmetry*.—Symmetric.
*Shape of base*.—Slightly depressed.
*Shape of apex*.—Slightly pointed.
Fruit stem cavity:
*Depth of stalk cavity*.—Shallow; Approximately 6 mm.
*Width of stalk cavity*.—Medium; Approximately 12 mm.
*Depth of suture*.—Absent.
Fruit skin:
*Thickness*.—Medium.
*Adherence to flesh*.—Strong.
*Surface texture*.—Smooth.
*Pubescence*.—None.
*Bloom*.—Medium.
*Ground color*.—Not visible.
*Overcolor*.—About Dark Greyed-Purple 187A, becoming fully Black 202A.
*Pattern of overcolor*.—Solid.
*Reticulation*.—Absent.
*Tendency to crack*.—Rare.
*Number of lenticels*.—Medium; about 7/cm$^2$.
*Size of lenticels*.—Very small and difficult to see; less than 0.5 mm.
Flesh:
*Ripens*.—Evenly.
*Texture*.—Firm-juicy.
*Flavor*.—Mildly sweet.
*Color*.—About Dark Red 53B.
*Firmness*.—Firm, typically 10-13 lb pressure to harvest.
*Juice*.—High, able to squeeze free juice easily.
*Acidity*.—Medium for plums, 0.46% titratable acidity.
*Sweetness*.—High, about 18 degrees btix at harvest.
*Adherence to stone*.—Semi-free.
*Amount of fiber*.—Low.
Fruit use: Fresh market.
Fruit shipping and keeping quality: Good.
Stone:
*Stone freeness*.—Semi-free.
*Stone size*.—Size: Medium. Length: Approximately 19 mm. Diameter in line with suture plan: Approximately 18 mm. Diameter perpendicular to suture plane: Approximately 8 mm.
*Color*.—About Medium Greyed-Yellow 161B when dried.
*Position of maximum diameter*.—Middle.
*Shape from lateral view*.—Circular.
*Shape from ventral view*.—Narrow elliptic.
*Shape from basal view*.—Narrow elliptic.
*Base shape*.—Nearly straight.
*Apex shape*.—Pointed.
*Stone ridgers*.—Rounded throughout.
*Stone outgrowing keel*.—Well developed.
*Ventrical edge*.—Thin with wing toward middle.
*Dorsal edge*.—Narrow, shallow grooves throughout.
*Fibers*.—Not visible.

*Symmetry in lateral view*.—Moderately asymmetrical.
*Texture of lateral surface*.—Rough.
*Width of stalk-end*.—Narrow.
*Tendency to split*.—Rare.

What is claimed is:

1. A new and distinct variety of plum tree as herein described and illustrated.

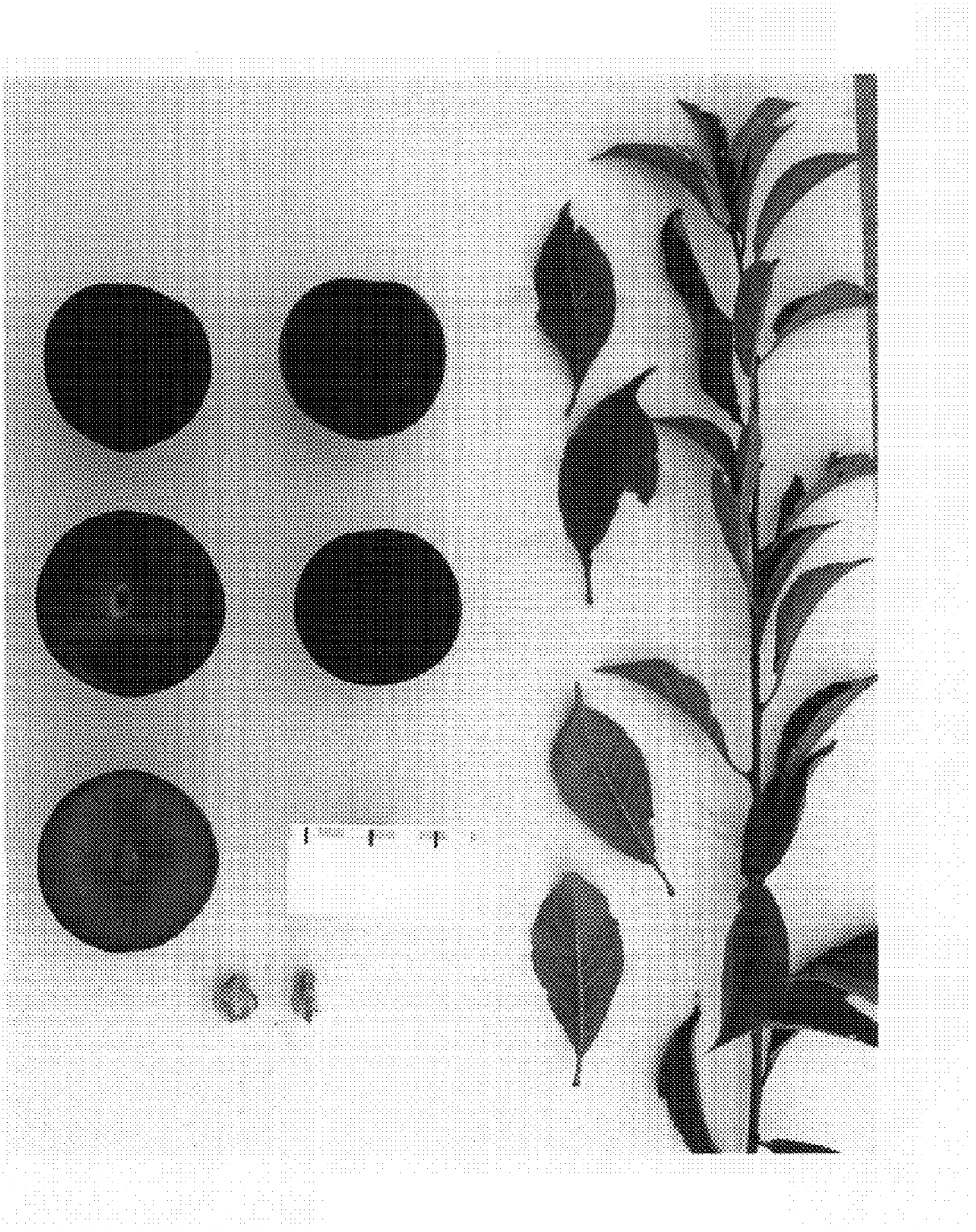

* * * * *